US008098165B2

(12) United States Patent
Demirdjian et al.

(10) Patent No.: US 8,098,165 B2
(45) Date of Patent: Jan. 17, 2012

(54) SYSTEM, APPARATUS AND ASSOCIATED METHODOLOGY FOR INTERACTIVELY MONITORING AND REDUCING DRIVER DROWSINESS

(75) Inventors: David Demirdjian, Somerville, MA (US); Chenna K. Varri, Quincy, MA (US)

(73) Assignee: Toyota Motor Engineering & Manufacturing North America (TEMA), Erlanger, KY (US)

( * ) Notice: Subject to any disclaimer, the term of this patent is extended or adjusted under 35 U.S.C. 154(b) by 352 days.

(21) Appl. No.: 12/394,125

(22) Filed: Feb. 27, 2009

(65) Prior Publication Data

US 2010/0219955 A1    Sep. 2, 2010

(51) Int. Cl.
*G08B 23/00* (2006.01)
(52) U.S. Cl. .................... 340/575; 340/691.1; 340/425.5
(58) Field of Classification Search .................. 340/575, 340/576, 439, 435, 438, 691.1, 901–903, 340/309.16, 309.4, 545.4, 436, 425.5
See application file for complete search history.

(56) References Cited

U.S. PATENT DOCUMENTS

| | | | |
|---|---|---|---|
| 3,922,665 A | 11/1975 | Curry et al. | |
| 4,158,198 A | 6/1979 | Ochiai | |
| 4,581,607 A * | 4/1986 | Seko et al. | 340/576 |
| 5,684,462 A | 11/1997 | Gold | |
| 6,154,123 A * | 11/2000 | Kleinberg | 340/436 |
| 6,426,702 B1 | 7/2002 | Young et al. | |
| 6,661,345 B1 * | 12/2003 | Bevan et al. | 340/575 |
| 6,822,573 B2 * | 11/2004 | Basir et al. | 340/575 |
| 7,196,629 B2 | 3/2007 | Ruoss et al. | |
| 7,295,123 B2 | 11/2007 | Engelberg et al. | |
| 7,400,259 B2 | 7/2008 | O'Connor et al. | |
| 7,477,758 B2 * | 1/2009 | Piirainen et al. | 382/100 |
| 2004/0133082 A1 | 7/2004 | Abraham-Fuchs et al. | |
| 2008/0103033 A1 | 5/2008 | Agarwal | |
| 2009/0027212 A1 * | 1/2009 | Nakagoshi et al. | 340/575 |
| 2010/0017466 A1 * | 1/2010 | Trauner | 709/203 |

* cited by examiner

*Primary Examiner* — Daniel Previl
(74) *Attorney, Agent, or Firm* — Oblon, Spivak, McClelland, Maier & Neustadt, L.L.P.

(57) ABSTRACT

A system, apparatus and associated methodology for interactively monitoring and reducing driver drowsiness use a plurality of drowsiness detection exercises to precisely detect driver drowsiness levels, and a plurality of drowsiness reduction exercises to reduce the detected drowsiness level. A plurality of sensors detect driver motion and position in order to measure driver performance of the drowsiness detection exercises and/or the drowsiness reduction exercises. The driver performance is used to compute a drowsiness level, which is then compared to a threshold. The system provides the driver with drowsiness reduction exercises at predetermined intervals when the drowsiness level is above the threshold.

20 Claims, 6 Drawing Sheets

SYSTEM, APPARATUS AND ASSOCIATED METHODOLOGY FOR INTERACTIVELY MONITORING AND REDUCING DRIVER DROWSINESS

BACKGROUND OF THE INVENTION

1. Field of the Invention

The present invention relates to a system, apparatus and associated methodology for interactively monitoring and detecting driver drowsiness. More specifically, the present invention relates to a system, apparatus and associated methodology that provide a driver with drowsiness detection exercises to determine the driver's drowsiness level, and provides the driver with drowsiness reduction exercises to reduce his or her drowsiness level.

2. Discussion of the Related Art

Each year drivers suffering from drowsiness cause numerous accidents on the nation's roadways. Drowsy drivers are less aware of their surroundings, and react more slowly than an alert driver. Even if a drowsy driver timely reacts, his or her reaction is often less precise than that of an alert driver. Thus, a drowsy driver is less able to handle quickly changing roadway conditions even if the driver is not in danger of actually falling asleep.

Drivers become drowsy for numerous reasons. For example, a driver may be suffering from lack of sleep, may be fatigued after a long-day's work, or may be under the influence of medications. Drivers may also become drowsy while driving late at night, driving for long stints without a break, or driving on a desolate road with little or no visual stimulation. Other factors that contribute to driver drowsiness include number of passengers, time of day, ambient lighting, temperature, etc.

Compounding the danger of driving while drowsy is a drowsy driver's inability to correctly assess his or her own level of drowsiness. Often drowsy drivers fail to recognize that their driving skills are markedly impaired, even at the point of falling asleep. Therefore, objective methods and systems are needed to detect drowsiness levels in drivers, and to reduce these drowsiness levels once detected.

One conventional way of detecting drowsiness uses cameras to analyze driver eye movements. Another conventional method uses a lamp installed at a conspicuous location on the car dashboard. The lamp is turned on at random time intervals, and the driver must turn the lamp off by pressing a button. Drowsiness is then detected by measuring the driver's response time. However, both of these conventional methods of detecting driver drowsiness are imprecise and prone to false positive readings (i.e. detecting driver drowsiness when the driver is actually alert), and neither quantify a driver's drowsiness level.

Other conventional methods focus on reducing driver drowsiness either independently, or in conjunction with one or both of the methods described above. One such conventional system adjusts the temperature within the vehicle once driver drowsiness is detected. Another conventional method employs an audible alarm that the driver must deactivate by pressing a deactivation button. A third conventional method does not attempt to detect driver drowsiness at all. Instead, the method merely provides the driver with a series of drowsiness reduction exercises at random time intervals, and leaves the driver to perform the exercises unchecked. As such, this conventional method is not able to determine an effectiveness of a given drowsiness reduction exercise, nor even if the driver is performing the exercise at all. Further, the one-way communication of this method may even allow the driver to ignore the system because driver input is not required.

Moreover, none of the above-described conventional methods quantify a driver drowsiness level, and therefore none of the above-described methods are capable of determining the effectiveness of their respective drowsiness counter measure. Thus, these conventional methods cannot adapt according to the drowsiness level of the driver, and cannot provide the driver with an array of different stimulus to stave off drowsiness. Instead, they merely provide a driver with the same stimulus (i.e. temperature variation and/or audible alarm) to counter drowsiness, even though such unchanging stimulus loses effect with each repeated application.

As first recognized by the present inventors, a need exists for a system that can precisely and interactively detect driver drowsiness in order to quantify the driver's drowsiness level, and that can provide a varied array of drowsiness reduction exercises to the driver based on the drowsiness level.

SUMMARY OF THE INVENTION

The present invention seeks to solve at least the above-noted problems through a system for monitoring and reducing driver drowsiness. The system includes a plurality of sensors that sense a driver's position and motion, and an electronic storage unit that stores an exercise database, which includes a plurality of drowsiness detection exercises and a plurality of drowsiness reduction exercises. The system also includes an input/output interface that transmits information to a driver and also receives information from the driver. A data processor, also included in the system, selects a drowsiness detection exercise from the exercise database and provides the drowsiness detection exercise to the driver via the input/output interface. Then the data processor monitors driver performance of the drowsiness detection exercise via the plurality of sensors, and generates a drowsiness level in accordance with the driver performance and a model performance of the drowsiness detection exercise. The data processor also provides a drowsiness reduction exercise to the driver at predetermined time intervals, and monitors the driver performance thereof, when the drowsiness level exceeds a predefined threshold.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE PREFERRED EMBODIMENTS

The present description describes preferred embodiments of the invention by referring to the accompanying drawings.

Figure 1:
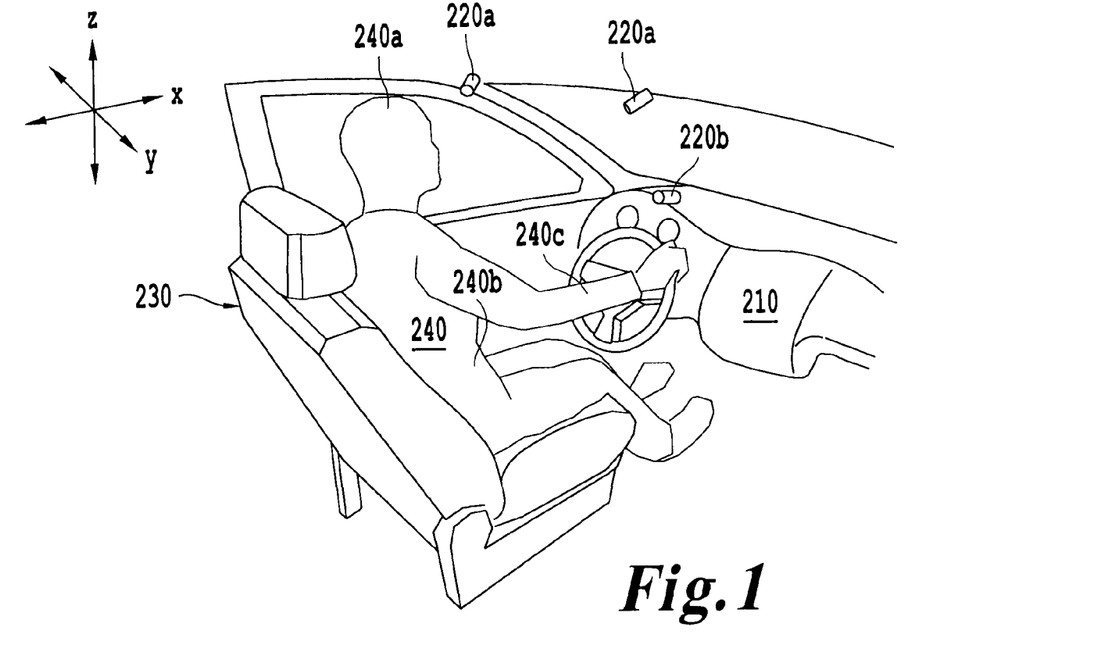
FIG. 1 is a perspective view of a driver seated in a car equipped with a drowsiness monitoring and reduction system according to an exemplary embodiment of the present invention.

FIG. 1 is a perspective view of a driver 240 seated in a vehicle 210 that is equipped with a drowsiness monitoring and reduction system according to an exemplary embodiment of the present invention. The driver 240 is seated on a driver seat 230 facing cameras 220a and 220b, which form part of the drowsiness monitoring and reduction system. The driver 240 may move his or her head 240a in any of an X, Y, and/or Z direction. Similarly, the driver's torso 240b and arm 240c may move in any of the Y, X and/or Z directions. The cameras 220a and 220b capture any motion from the driver's head 240a, torso 240b and/or arm 240c for processing and analysis by the drowsiness monitoring and reduction system.

Figure 2:
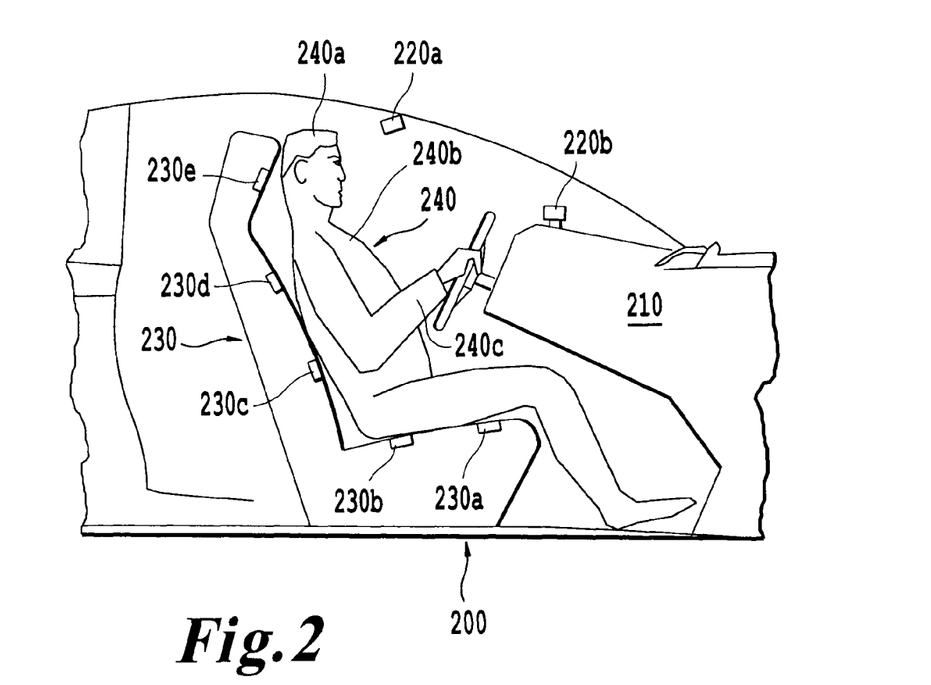
FIG. 2 is a diagram of the driver seated in the car equipped with the drowsiness monitoring and reduction system according to the exemplary embodiment of the present invention.

FIG. 2 is a two-dimensional diagram of the driver 240 inside the vehicle 210 equipped with the drowsiness monitoring and reduction system according to the exemplary embodiment of the present invention. In FIG. 2, pressure sensors 230a, 230b, 230c, 230d and 230e record a pressure exerted by the driver on the driver seat 230 in order to further define driver motion and position, along with cameras 220a and 220b.

Though FIG. 2 includes both cameras (220a and 220b) and pressure sensors (230a, 230b, 230c, 230d and 230e) to determine driver position and motion, one of skill in the art will readily appreciate that only cameras or only pressure sensors may be used without departing from the scope of the present invention. Likewise, the number of cameras and their respective position in FIG. 2 are merely exemplary, and therefore not limiting of the present invention. Any number of cameras may be used. The present invention also accommodates any number of pressure sensors positioned at any location on the driver seat 230. Other sensors, such as infrared sensors, accelerometers, etc. are also accommodated by the present invention, as one of ordinary skill in the art will readily appreciate.

Figure 3:
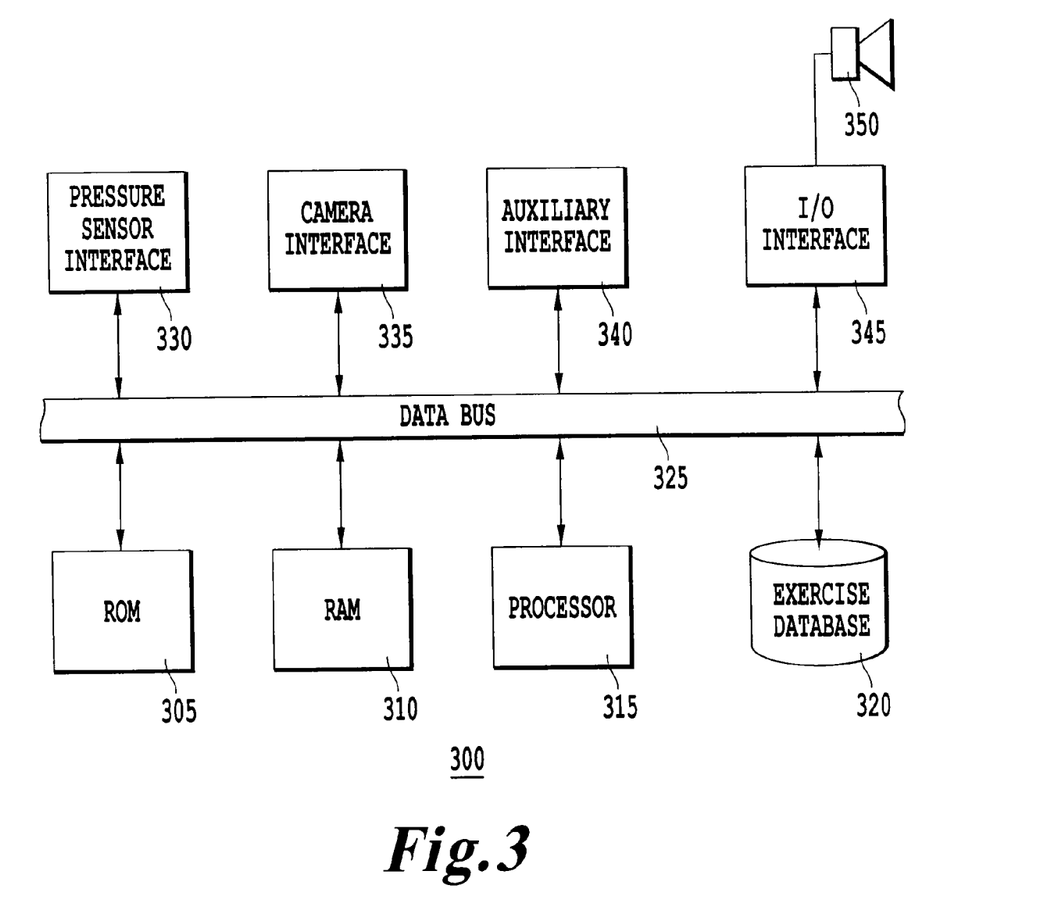
FIG. 3 is a block diagram of the drowsiness monitoring and reduction system according to the exemplary embodiment of the present invention.

FIG. 3 is a block diagram of a system for monitoring and reducing driver drowsiness according to the exemplary embodiment of the present invention. The system 300 includes a processor 315, an exercise database 320, random access memory (RAM) 310, read only memory (ROM) 305, a pressure sensor interface 330, a camera interface 335, an auxiliary interface 340, and an input/output (I/O) interface 345 connected to a sound source 350. The system 300 also includes a data bus 325 that interconnects the above-described components.

The pressure sensors interface 330 collects driver position and motion information from the pressure sensors 230a, 230b, 230c, 230d and 230e and places it on the data bus 325. The processor 315 retrieves the driver position and motion information from the data bus 325 and uses it to monitor driver drowsiness levels. Similarly, the processor 315 may retrieve information placed on the data bus 325 by cameras 220a and 220b via the camera interface 335. The input/output interface 345 transmits information placed on the data bus 325 by the processor 315 to the sound source 350 for reproduction to the driver 240.

Though only a sound source 350 is shown in FIG. 3, the present invention is not limited only to audio driver feedback. A display (not shown) may also be connected to the input/output interface 345 to provide a visual display to the driver, as will be described below. A user input device may also be connected to the input/output interface 345 for transmitting user input to the processor 315 by way of the data bus 325.

The ROM 305 stores program instructions, which are executed by the processor 315 to perform the method described below, and the RAM 310 is used to temporarily store information as needed. Information stored in RAM 310 includes, computational variables, driver data, a table of administered exercises, environmental variables, and any other temporarily stored information known in the art. Further, the RAM 310 may be any one of EEPROM, non-volatile RAM, static RAM, dynamic RAM, FLASH memory, and any other electronic storage media known in the art.

The exercise database 320 stores a plurality of drowsiness detection exercises and a plurality of drowsiness reduction exercises, and may be implemented as a hard disk drive, FLASH memory, optical drive, CD-ROM, DVD disk, and the like. In this context, a drowsiness detection exercise is an exercise that aids the system in detecting a driver's drowsiness level. For example, a drowsiness detection exercise may include setting a dial to a particular setting, extending the driver's right arm 240c fully, adjusting the vehicle's radio to a given setting, and the like. A drowsiness reduction exercise is an exercise designed to increase blood flow in the driver. For example, drowsiness reduction exercises may include stretching, rotating the driver's head 240a, exercising the driver's torso 240b, and the like.

Both the drowsiness detection exercises and the drowsiness reduction exercises may be divided into categories to optimize drowsiness detection and reduction (as described below). For example, these exercises may be grouped into categories according to body parts, such as head exercises, torso exercises and limb exercises. However, other categories are possible, such as difficulty level, effectiveness level, etc. Thus, the above-mentioned categories are merely exemplary and do not limit the scope of the present invention.

The auxiliary interface 340 may be used to interface additional sensors, such as ambient light sensors, temperature sensors, time sensors, and/or an accelerometer attached to the driver's seatbelt. Information from these sensors may be used to further refine the detection of driver drowsiness. As can be appreciated by one skilled in the art, the above-listed sensors are merely exemplary, and other sensors are possible. Therefore, the above-listed sensors are not limiting of the scope of the present invention.

The drowsiness reduction system 300 of FIG. 3 may be implemented as a standalone apparatus, or may be implemented within an existing vehicle system. Further, the processor 315 may be implemented as a general purpose microprocessor or may also be implemented as an FPGA, CPLD, ASIC, or specialized microprocessor as can be appreciated by those skilled in the art.

Moreover, the method described below may be implemented on the above-described processor 315 as software instructions provided in the form of a utility application, background daemon, component of an operating system, or any combination thereof, executing in conjunction with the processor 315 and an operating system such as Microsoft VISTA, Unix, Solaris, Linux, Apple MAC-OS and other systems known to those skilled in the art.

Figure 4:
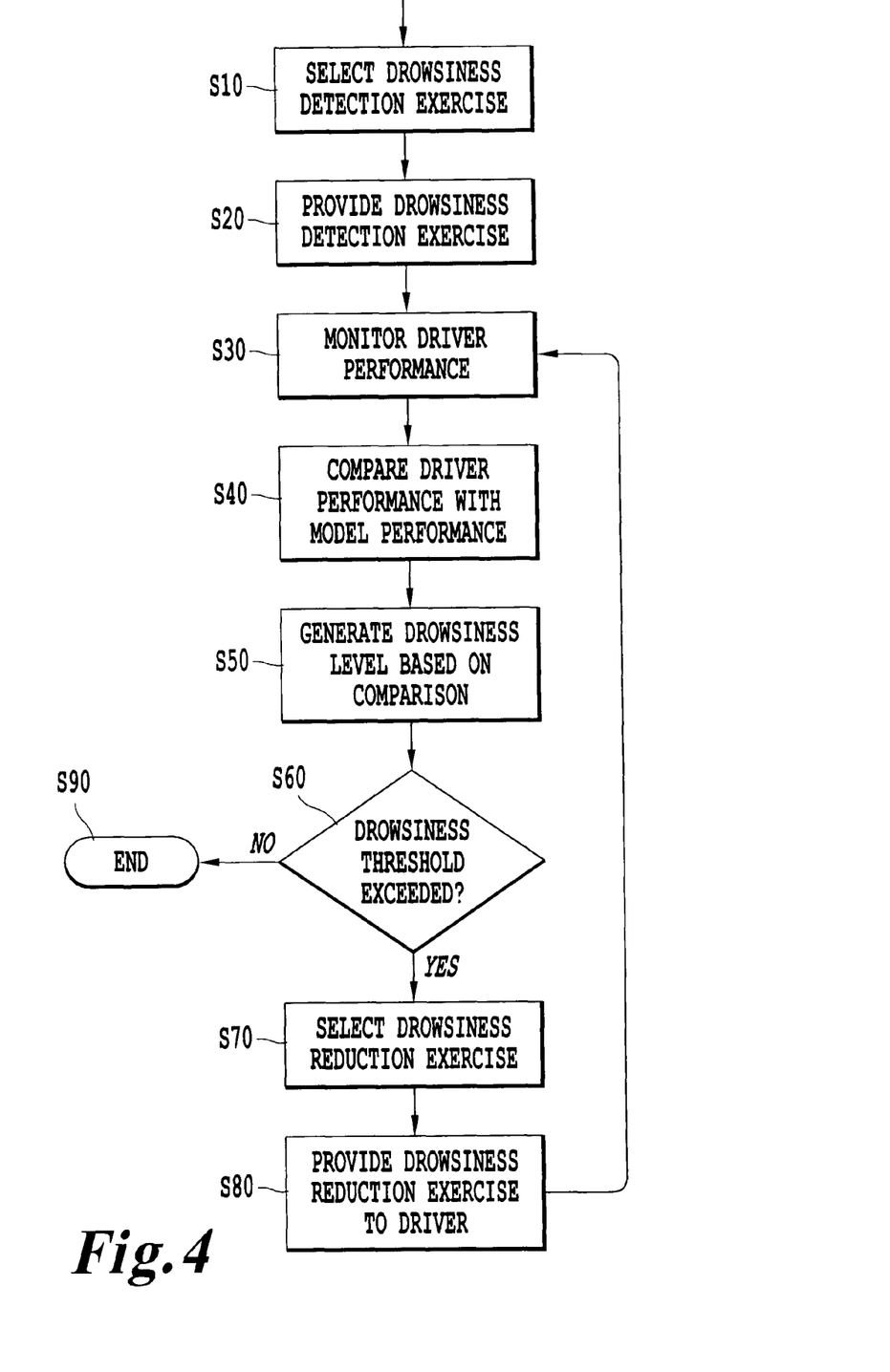
FIG. 4 is a flowchart of a drowsiness monitoring and reduction method according to the exemplary embodiment of the present invention.

Next a method for monitoring and reducing driver drowsiness is described with reference to FIG. 4. At step S10 the method selects a drowsiness detection exercise from the exercise database, such as exercise database 320 of FIG. 3. The exercise may be selected at random, by a statistical measure of its effectiveness in detecting drowsiness, or any other selection criteria known in the art. The exercise may also be chosen based on its past efficacy with the particular driver being tested.

At step S20 the method provides the drowsiness detection exercise to the driver. Such provision of the drowsiness detection exercise may be by way of the sound source 350, a visual display, or any other method known in the art.

Once the drowsiness detection exercise has been provided to the driver, the method monitors driver performance of the exercise at step S30. Then driver performance is compared to a model performance of the exercise at step S40. In this context, a model performance of the exercise includes a statistical mean of a plurality of driver performances of the exercise, a theoretical model of the exercise performance, an individual model pertaining to the particular driver being tested, or any other such model known in the art.

At step S50 the method generates a drowsiness level based on the comparison of step S40. In this context, a drowsiness level refers to the level of fatigue and/or lethargy experienced by the driver, which results in impairment of driving ability. As such, a high level of drowsiness indicates a high degree of driving ability impairment, and a low drowsiness level indicates a low degree of impairment.

At step S60, the drowsiness level is compared to a drowsiness threshold. If the drowsiness level exceeds the drowsiness threshold, the method proceeds to step S70 where it selects a drowsiness reduction exercise from the database 320. The drowsiness threshold may be a statistical level at which the average driver exhibits markedly impaired driving ability, or maybe specific to the particular driver being tested.

At step S80 the method provides the drowsiness reduction exercise to the driver, and reverts to step S30 to monitor driver performance of the drowsiness reduction exercise. Steps S40 and S50 are used to generate a new drowsiness level corresponding to the drowsiness reduction exercise and this new drowsiness level is compared to the drowsiness threshold at step S60.

The method continues looping from steps S30 through steps S80 to provide a drowsiness reduction exercise to the driver at predetermined time intervals while the drowsiness threshold is exceeded. Any time interval may be used. For example, steps S30 through S80 may take one minute to perform, thereby providing new drowsiness reduction exercises to the driver every minute. A delay may also be introduced to provide the drowsiness reduction exercises to the driver at periods longer than one minute. Alternatively, the drowsiness reduction exercises may be provided to the driver at time intervals that are shorter than one minute. Therefore, the time intervals described above are merely exemplary and do not limit the scope of the present invention.

If, at step S60, the drowsiness level does not exceed the drowsiness threshold, the method ends. However, the method may administer at least a drowsiness detection exercise to the driver upon the occurrence of a predetermined event. Such predetermined events may include the expiration of a timer, a predetermined drive time, a predetermined ambient light temperature, at random or any other triggering event known in the art.

Figure 5:
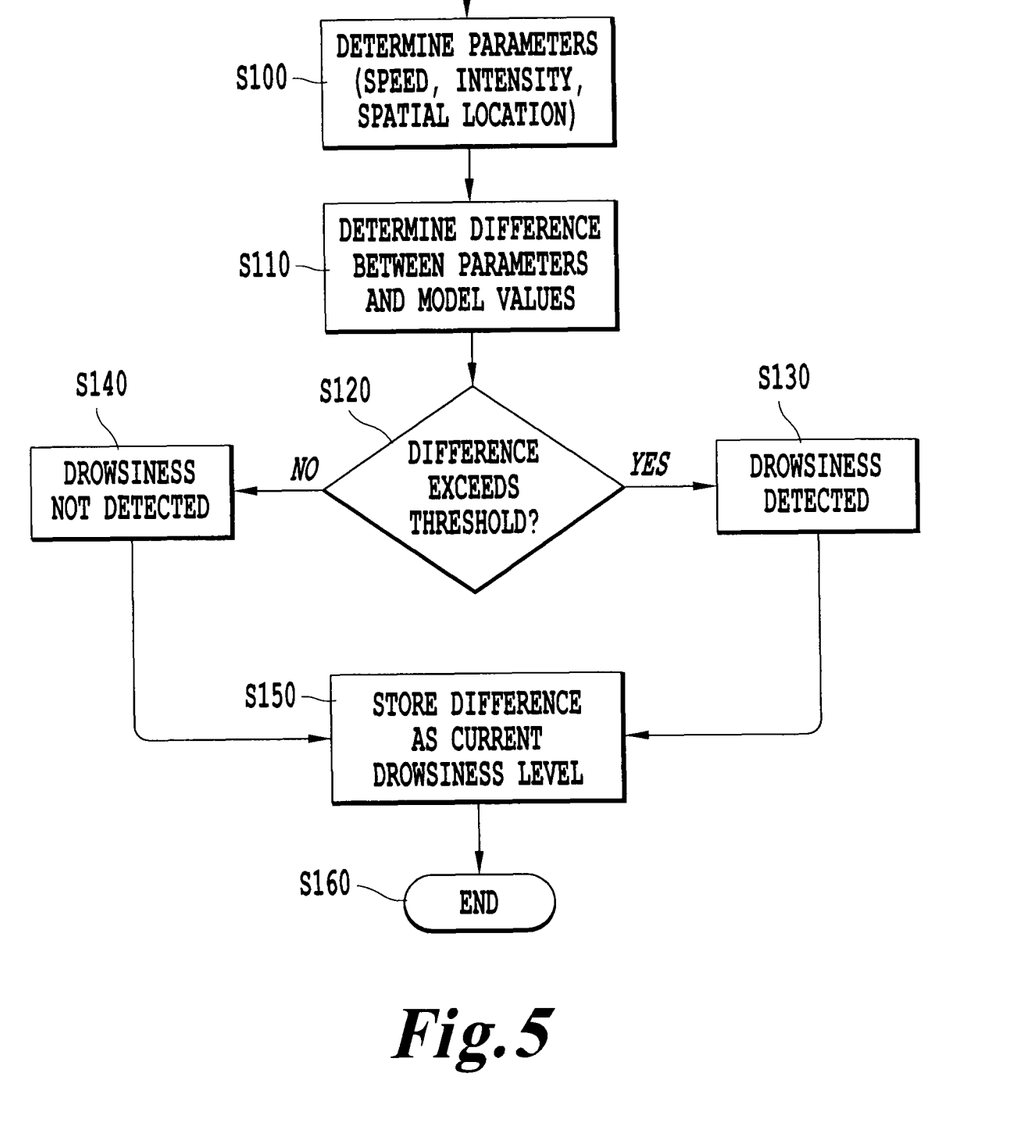
FIG. 5 is a flowchart of determining a drowsiness level according to the exemplary embodiment of the present invention.

FIG. 5 is a flowchart of drowsiness level determination according to an exemplary embodiment of the present invention. At step S100, the method determines a set of parameters including the velocity of a limb, the intensity of movement, and the spatial location of the limb. In this context a limb may be the driver's head 240a, torso 240b, arm 240c, or any combination thereof. Then, at step S110, the method determines a difference between the parameters and a model set of parameter values corresponding to the model performance described above. This difference corresponds to the drowsiness level, and is then compared to the drowsiness threshold at step S120 to determine whether drowsiness is detected.

The difference corresponding to drowsiness level may also be determined as a group of differences, each corresponding to one of the above-described parameters. Alternatively, the difference corresponding to drowsiness level may be computed as an average of the above-described differences, sum of the above-described differences, or any other mathematical combination known in the art. Likewise, the drowsiness threshold at step S120 may be a single threshold that is compared against one of the above-described combinations, or may be a plurality of individual thresholds corresponding to each of the above-described parameters for comparison to each parameter individually. Thus, drowsiness may be detected by exceeding an overall threshold, by exceeding an individual threshold, by exceeding a predetermined number of individual thresholds, or any combination thereof. One of skill in the art will appreciate that other functions can be used to detect drowsiness levels without departing from the scope of the present invention.

If drowsiness is detected, the method moves to step S130 where administration of drowsiness reduction exercises is performed as discussed above. At step S150, the difference corresponding to drowsiness level is stored as the current drowsiness level in RAM 310. However, the current drowsiness level may also be stored in other electronic storage media, such as a hard disk drive, FLASH, EEPROM, CD-ROM, and any other storage media known in the art. If drowsiness is not detected, the method moves to step S140, which bypasses administration of a drowsiness reduction exercise and proceeds to step S150 for storage of the current drowsiness level. The method ends at step S160.

Figure 6:
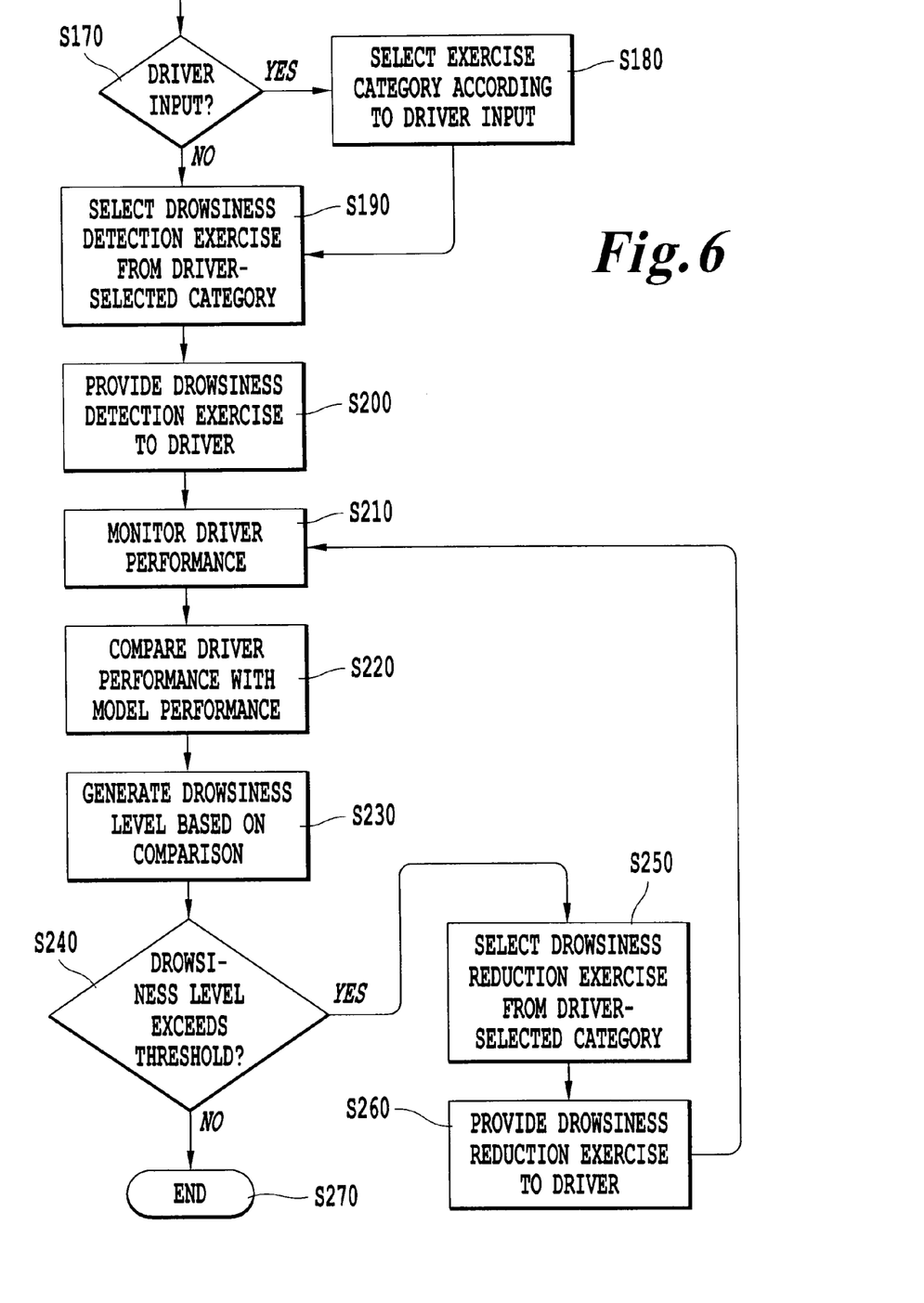
FIG. 6 is a flowchart of a drowsiness monitoring and reduction method according to another exemplary embodiment of the present invention.

Next, another embodiment of a method for monitoring and reducing driver drowsiness will be explained with reference to FIG. 6. In FIG. 6, the method begins by determining whether driver input is received at step S170. If driver input is received the method proceeds to step S180 where a category of exercise is selected according to the driver input. Then at step S190, the method selects a drowsiness detection exercise from the driver-selected category. Steps S200 through S270 correspond to steps S20 through S90 of FIG. 4, and therefore will not be discussed for the sake of brevity.

If user input is not detected at step S170, the method proceeds directly to step S190 where a drowsiness detection exercise is selected from the last driver-selected category, or if no driver-selected category exists from a default category. Then the method performs steps S200 through S270.

Figure 7:
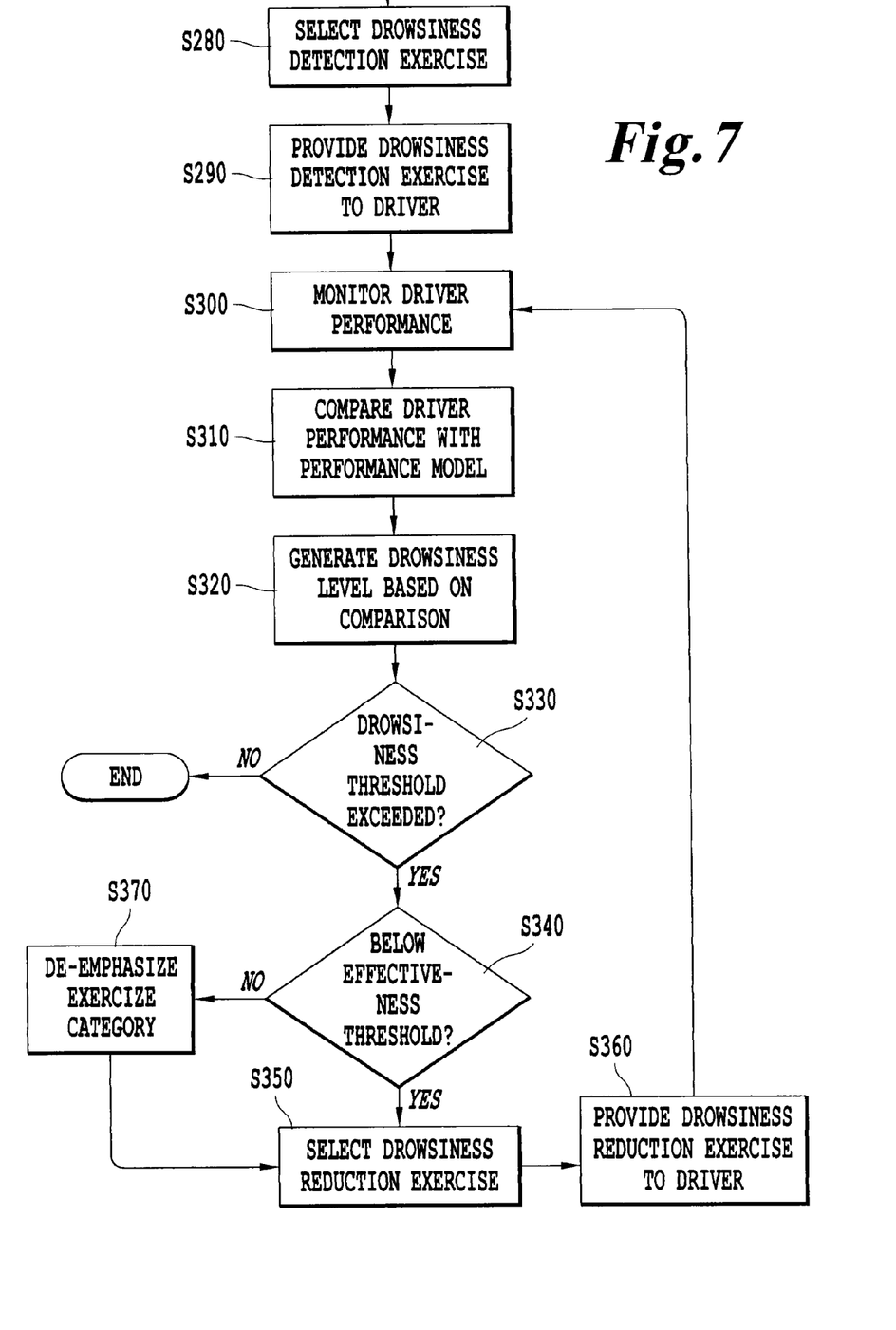
FIG. 7 is a flowchart of a drowsiness monitoring and reduction method according to a further exemplary embodiment of the present invention.

A further embodiment of the method for monitoring and reducing driver drowsiness is described with reference to FIG. 7, wherein Steps S280-S330, S350-360 and S380 correspond to steps S10-S80 of FIG. 4. At step S340 the method compares the drowsiness level to an effectiveness threshold. If the drowsiness level is below the effectiveness threshold the method continues to steps S350 and S360. However, if the drowsiness level is above the effectiveness threshold, the exercise category corresponding to the last-administered exercise is deemphasized at step S370. In this context, deemphasizing a category includes reducing a numeric rating of the category, removing the category from a table from which categories are selected, lowering the category's ranking, etc. On further iterations, the method may select exercises only from categories that are not deemphasized, or may select exercises from a deemphasized category less frequently. For example, the method may select exercises only from those categories having a highest numeric rating, or from categories whose numeric rating exceeds a predetermined threshold, or from categories contained in a category list. Alternatively, the method may skip a deemphasized category for a predetermined number of iterations (i.e. 2) before selecting an exercise from that category. However, other methods of deemphasizing categories are possible without departing from the scope of the present invention.

Further, the above embodiments may also include providing the driver with a visual display of the driver's current drowsiness level. This visual display may take the form of a numeric display, a graphical display, or any combination thereof.

The above-described embodiments of the present invention may also include monitoring driver performance of a drowsiness detection exercise or a drowsiness reduction exercise when the driver is known to be alert. This alert performance of the exercise may be used as a baseline to adjust the model performance of the exercise. The system may then generate the drowsiness level according to the adjusted model performance. As used in this context, an alert driver performance may also include a non-drowsy driver performance, a normal driver performance, a baseline driver performance, a reference driver performance, and/or a typical driver performance.

Several flowcharts are used in the above description. However, any processes, descriptions or blocks in the flowcharts should be understood as representing modules, segments, portions of code which include one or more executable instructions for implementing the specific logical function or steps in the process, and alternate implementations are included within the scope of the exemplary embodiment of the present invention in which functions may be executed out of order from that shown or discussed, including substantially concurrently or in reverse order, depending upon the functionality involved, as would be understood by those skilled in the art.

Moreover, the foregoing discussion discloses merely exemplary embodiments of the present invention. As will be understood by those skilled in the art, the present invention may be embodied in other specific forms without departing from the spirit or essential characteristics thereof. Accordingly, the disclosure of the present invention is intended to be illustrative, but not limiting of the scope of the invention, as well as other claims. The disclosure, including any readily discernible variance of the teachings herein, define, in part, the scope of the foregoing terminology such that no inventive subject matter is dedicated to the public.

The invention claimed is:

1. A system for monitoring and reducing driver drowsiness, comprising:
   a plurality of sensors configured to sense driver position and motion;
   an electronic storage unit configured to store an exercise database including a plurality of drowsiness detection exercises and a plurality of drowsiness reduction exercises;
   an input/output interface configured to transmit information to a driver, and configured to receive information from the driver; and
   a data processor configured to
      select a drowsiness detection exercise from the exercise database,
      instruct the drowsiness detection exercise to the driver via the input/output interface,
      monitor driver performance of the instructed drowsiness detection exercise via the plurality of sensors,
      generate a drowsiness level by comparing the driver performance of the instructed drowsiness detection exercise to a model performance of the instructed drowsiness detection exercise, and
      compare the drowsiness level to a predetermined threshold,
   wherein the data processor instructs a drowsiness reduction exercise to the driver at predetermined time intervals and monitors driver performance thereof, when the drowsiness level exceeds a predetermined threshold.

2. The system for monitoring and reducing driver drowsiness according to claim 1, wherein the data processor generates parameters including at least one of an exercise intensity, a limb velocity and a limb spatial position based on the driver performance, and generates the drowsiness level by comparing the generated parameters to parameters corresponding to the model performance.

3. The system for monitoring and reducing driver drowsiness according to claim 1, wherein the data processor stores a non-drowsy driver performance in an electronic memory, and adjusts the model performance based on the non-drowsy driver performance, the drowsiness level being generated based on the adjusted model performance.

4. The system for monitoring and reducing driver drowsiness according to claim 1, wherein the input/output interface receives an exercise category selection, and the data processor selects drowsiness detection exercises and drowsiness reduction exercises from the selected category.

5. The system for monitoring and reducing driver drowsiness according to claim 1, wherein the input/output interface receives an exercise category rejection, and the data processor selects drowsiness detection exercises and drowsiness reduction exercises from categories other than the rejected category.

6. The system for monitoring and reducing driver drowsiness according to claim 1, wherein the plurality of sensors include at least one of a plurality of pressure sensors arranged on a driver seat and a plurality of cameras facing the driver seat.

7. The system for monitoring and reducing driver drowsiness according to claim 6, wherein the plurality of sensors also includes an accelerometer arranged on a driver seatbelt.

8. The system for monitoring and reducing driver drowsiness according to claim 1, further comprising:
   a display unit connected to the input/output interface and configured to provide a current drowsiness level to the driver.

9. A system for monitoring and reducing driver drowsiness, comprising:
   a plurality of sensors configured to sense driver position and motion;
   an electronic storage unit configured to store an exercise database including a plurality of drowsiness detection exercises and a plurality of drowsiness reduction exercises;
   an input/output interface configured to transmit information to a driver, and configured to receive information from the driver; and
   a data processor configured to select a drowsiness detection exercise from the exercise database, and configured to provide the drowsiness detection exercise to the driver via the input/output interface, the data processor monitoring driver performance of the drowsiness detection exercise via the plurality of sensors and generating a drowsiness level in accordance with the driver performance and a model performance of the drowsiness detection exercise, wherein the data processor provides a drowsiness reduction exercise to the driver at predetermined time intervals and monitors driver performance thereof, when the drowsiness level exceeds a predetermined threshold, and wherein the data processor compares a drowsiness level, corresponding to an exercise, to an effectiveness threshold, and deemphasizes a category corresponding to the exercise when the drowsiness level is below the effectiveness threshold, the data processor selecting a further exercise from a category other than the deemphasized category, the exercise and the further exercise being one of a drowsiness detection exercise and a drowsiness reduction exercise.

10. A method for monitoring and reducing driver drowsiness, comprising:

selecting, from an exercise database stored in an electronic storage unit, a drowsiness detection exercise, the database including a plurality of drowsiness detection exercises and a plurality of drowsiness reduction exercises;

instructing, via an input/output interface, the drowsiness detection exercise to a driver;

monitoring, via a plurality of sensors, driver performance of the instructed drowsiness detection exercise;

determining, in a data processor, a drowsiness level based on a comparison of the driver performance of the instructed drowsiness detection exercise with a model performance of the drowsiness detection exercise; and comparing the drowsiness level to a drowsiness threshold, wherein a drowsiness reduction exercise is instructed to the driver at predetermined time intervals when the drowsiness level is above the drowsiness threshold.

11. The method of monitoring and reducing driver drowsiness according to claim 10, further comprising:

generating parameters including at least one of an exercise intensity, a limb velocity and a limb spatial location based on the driver performance;

comparing the generated parameters to a model set of parameters corresponding to the model performance; and generating a drowsiness level based on the difference between the generated parameters and the model set of parameters.

12. The method of monitoring and reducing driver drowsiness according to claim 10, further comprising:

monitoring non-drowsy driver performance;

storing the non-drowsy driver performance in the electronic storage unit; and adjusting the model performance based on the non-drowsy driver performance, wherein the drowsiness level is computed based on the adjusted model performance.

13. The method of monitoring and reducing driver drowsiness according to claim 10, further comprising:

receiving a driver input via the input/output interface;

selecting at least one of a drowsiness detection exercise and a drowsiness reduction exercise from a selected category, when the driver input is a category selection; and selecting at least one of a drowsiness detection exercise and a drowsiness reduction exercise from a category other than a rejected category, when the driver input is a category rejection.

14. The method for monitoring and reducing driver drowsiness according to claim 10, further comprising:

displaying, on a display unit, a current drowsiness level.

15. A method for monitoring and reducing driver drowsiness, comprising:

selecting, from an exercise database stored in an electronic storage unit, a drowsiness detection exercise, the database including a plurality of drowsiness detection exercises and a plurality of drowsiness reduction exercises;

providing, via an input/output interface, the drowsiness detection exercise to a driver;

monitoring, via a plurality of sensors, driver performance of the drowsiness detection exercise;

determining, in a data processor, a drowsiness level based on the driver performance and a model performance of the drowsiness detection exercise;

comparing the drowsiness level to a drowsiness threshold, a drowsiness reduction exercise being provided to the driver at predetermined time intervals when the drowsiness level is above the drowsiness threshold determining an exercise effectiveness for an exercise based on a drowsiness level corresponding thereto; and de-emphasizing an exercise category corresponding to the exercise when the exercise effectiveness is below a predetermined effectiveness threshold, wherein a further exercise is selected from exercise categories other than the de-emphasized category, the exercise and the further exercise being one of a drowsiness detection exercise and a drowsiness reduction exercise.

16. An apparatus for monitoring and reducing driver drowsiness, comprising:

means for storing an exercise database including a plurality of drowsiness detection exercises and a plurality of drowsiness reduction exercises;

means for selecting a drowsiness detection exercise from the drowsiness detection exercise from the exercise database;

means for instructing the drowsiness detection exercise to a driver;

means for monitoring driver performance of the instructed drowsiness detection exercise;

means for generating a drowsiness level by comparing the driver performance of the instructed drowsiness detection exercise to a model performance of the drowsiness detection exercise;

means for comparing the drowsiness level to a predetermined threshold; and means for instructing a drowsiness reduction exercise to the driver at predetermined time intervals when the drowsiness level exceeds a predetermined drowsiness threshold.

17. The apparatus for monitoring and reducing driver drowsiness according to claim 16, further comprising:

means for deriving parameters including at least one of an exercise intensity, a limb velocity and a limb spatial position from the driver performance;

means for generating the drowsiness level based on the derived parameters and a model set of parameters derived from the model performance.

18. The apparatus for monitoring and reducing driver drowsiness according to claim 16, further comprising:

means for storing a non-drowsy driver performance; and means for adjusting the model performance based on the non-drowsy driver performance, wherein the drowsiness level is generated based on the adjusted model performance.

19. The apparatus for monitoring and reducing driver drowsiness according to claim 16, further comprising:

means for receiving a driver input, wherein at least one of a drowsiness detection exercise and a drowsiness reduction exercise is selected from a selected category, when the driver input indicates the selected category, and at least one of a drowsiness detection exercise and a drowsiness reduction exercise is selected from a category other than a rejected category, when the driver input indicates the rejected category.

20. An apparatus for monitoring and reducing driver drowsiness, comprising:

means for storing an exercise database including a plurality of drowsiness detection exercises and a plurality of drowsiness reduction exercises;

means for selecting a drowsiness detection exercise from the drowsiness detection exercise from the exercise database;

means for providing the drowsiness detection exercise to a driver;

means for monitoring driver performance of the drowsiness detection exercise;

means for generating a drowsiness level based on the driver performance and a model performance of the drowsiness detection exercise;

means for providing a drowsiness reduction exercise to the driver at predetermined time intervals when the drowsiness level exceeds a predetermined drowsiness threshold;

means for determining an exercise effectiveness corresponding to an exercise provided to the driver, the exercise effectiveness being determined in accordance with the drowsiness level; and means for de-emphasizing an exercise category corresponding to the exercise when the exercise effectiveness is below a predetermined effectiveness threshold, wherein a further exercise is selected from categories other than the de-emphasized category, the exercise and the further exercise being one of a drowsiness detection exercise and a drowsiness reduction exercise.

* * * * *